(12) United States Patent
Edwards et al.

(10) Patent No.: US 9,381,032 B2
(45) Date of Patent: Jul. 5, 2016

(54) SURGICAL INSTRUMENT WITH MALLEABLE TUBING

(71) Applicant: GYRUS ENT, L.L.C., Bartlett, TN (US)

(72) Inventors: Kevin C. Edwards, Olive Branch, MS (US); Michael J. Bennett, Bartlett, TN (US)

(73) Assignee: GYRUS ENT, L.L.C., Bartlett, TN (US)

( * ) Notice: Subject to any disclaimer, the term of this patent is extended or adjusted under 35 U.S.C. 154(b) by 0 days.

(21) Appl. No.: 14/925,387

(22) Filed: Oct. 28, 2015

(65) Prior Publication Data
US 2016/0045215 A1    Feb. 18, 2016

Related U.S. Application Data

(63) Continuation of application No. 13/216,714, filed on Aug. 24, 2011, now Pat. No. 9,198,685.

(51) Int. Cl.
*A61B 17/32* (2006.01)
*A61B 17/00* (2006.01)

(52) U.S. Cl.
CPC . *A61B 17/32002* (2013.01); *A61B 2017/00867* (2013.01); *A61B 2017/00946* (2013.01); *A61B 2017/00986* (2013.01); *A61B 2017/320032* (2013.01)

(58) Field of Classification Search
CPC ............... A61B 2017/00867; A61B 17/32002
USPC ......................................... 606/1, 80, 170, 130
See application file for complete search history.

(56) References Cited

U.S. PATENT DOCUMENTS

| 4,646,738 | A | 3/1987 | Trott |
| 5,707,350 | A | 1/1998 | Krause et al. |
| 5,749,357 | A | 5/1998 | Linder |
| 5,766,196 | A | 6/1998 | Griffiths |
| 5,833,692 | A | 11/1998 | Cesarini et al. |
| 5,922,003 | A | 7/1999 | Anctil et al. |

(Continued)

FOREIGN PATENT DOCUMENTS

| JP | H07-265325 A | 10/1995 |
| JP | 2003-220067 A | 8/2003 |

(Continued)

OTHER PUBLICATIONS

Feb. 17, 2015 Office Action issued in Japanese Application No. 2014-526082.

(Continued)

*Primary Examiner* — William Thomson
*Assistant Examiner* — Jeffrey Lipitz
(74) *Attorney, Agent, or Firm* — Oliff PLC

(57) ABSTRACT

A surgical instrument includes a hollow cylindrical member having a flexible region along at least a part of the hollow cylindrical member and a malleable tubing disposed over at least an outer surface of the flexible region of the hollow cylindrical member. The flexible region and the malleable tubing disposed over the flexible region can bend multiple times. The malleable tubing can maintain a bent orientation until the malleable tubing is re-bent by a user. The surgical instrument also includes connections that prevent the malleable tubing from moving longitudinally relative to the hollow cylindrical member. The malleable tubing may be made of various materials, one example of which is anodized, annealed aluminum.

21 Claims, 11 Drawing Sheets

(56) References Cited

U.S. PATENT DOCUMENTS

| | | |
|---|---|---|
| 6,461,363 B1 | 10/2002 | Gadberry et al. |
| RE38,018 E | 3/2003 | Anctil et al. |
| 6,620,180 B1 | 9/2003 | Bays et al. |
| 7,244,263 B2 | 7/2007 | Robison et al. |
| 7,247,161 B2 | 7/2007 | Johnston et al. |
| 7,699,846 B2 | 4/2010 | Ryan |
| 2003/0078644 A1 | 4/2003 | Phan |
| 2003/0236549 A1 | 12/2003 | Bonadio et al. |
| 2004/0064173 A1 | 4/2004 | Hine et al. |
| 2006/0111696 A1 | 5/2006 | Auld |
| 2009/0088728 A1 | 4/2009 | Dollar et al. |
| 2010/0087711 A1 | 4/2010 | Edwards |
| 2012/0221035 A1 | 8/2012 | Harvey |

FOREIGN PATENT DOCUMENTS

| | | |
|---|---|---|
| WO | 96/25103 A1 | 8/1996 |
| WO | 98/11832 A1 | 3/1998 |
| WO | 98/17187 A1 | 4/1998 |
| WO | 99/23958 A1 | 5/1999 |
| WO | 01/22889 A1 | 4/2001 |
| WO | 2008/031245 A2 | 3/2008 |
| WO | 2012/060959 A2 | 5/2012 |

OTHER PUBLICATIONS

Aug. 5, 2015 Office Action issued in Chinese Application No. 201280036150.7.

Dec. 1, 2014 Office Action issued in Australian Application No. 2012299289.

Feb. 27, 2015 Office Action issued in U.S. Appl. No. 13/216,714.

Jul. 14, 2015 Office Action issued in U.S. Appl. No. 13/216,714.

Sep. 17, 2015 Notice of Allowance issued in U.S. Appl. No. 13/216,714.

Oct. 15, 2012 International Search Report issued in PCT/US2012/050160.

Oct. 15, 2012 Written Opinion issued in PCT/US2012/050160.

Jul. 24, 2014 Office Action issued in Australian Patent Application No. 2012299289.

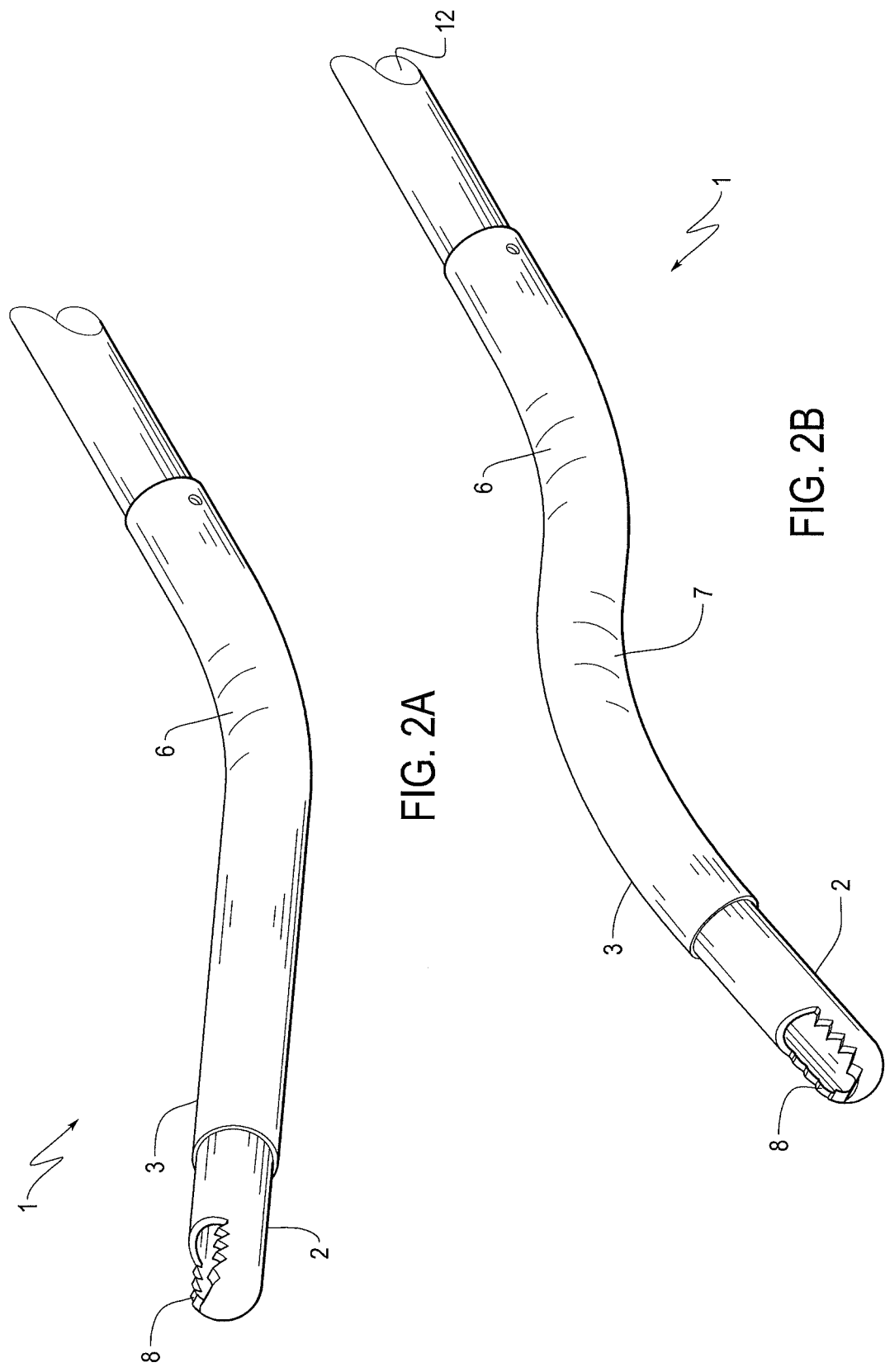

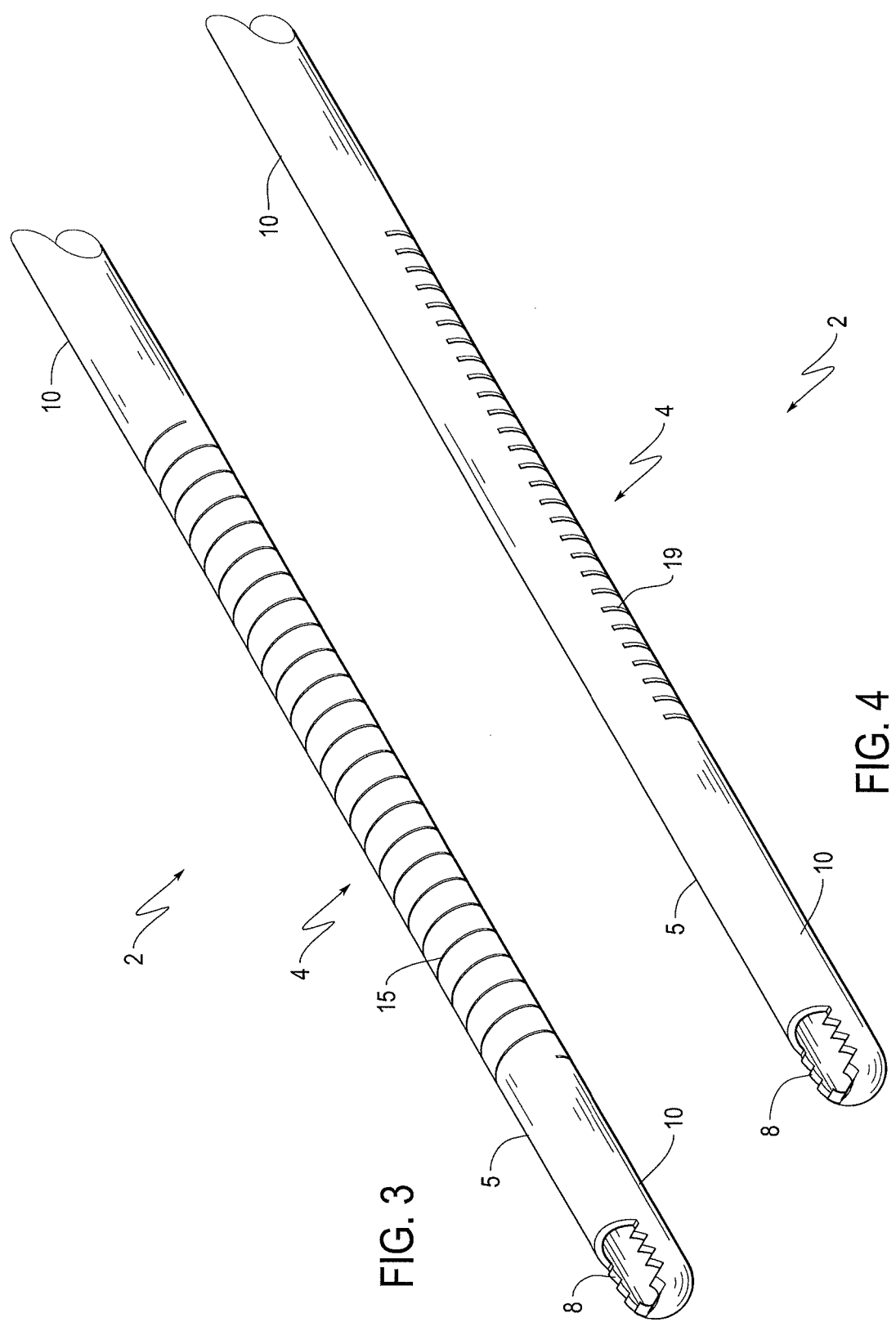

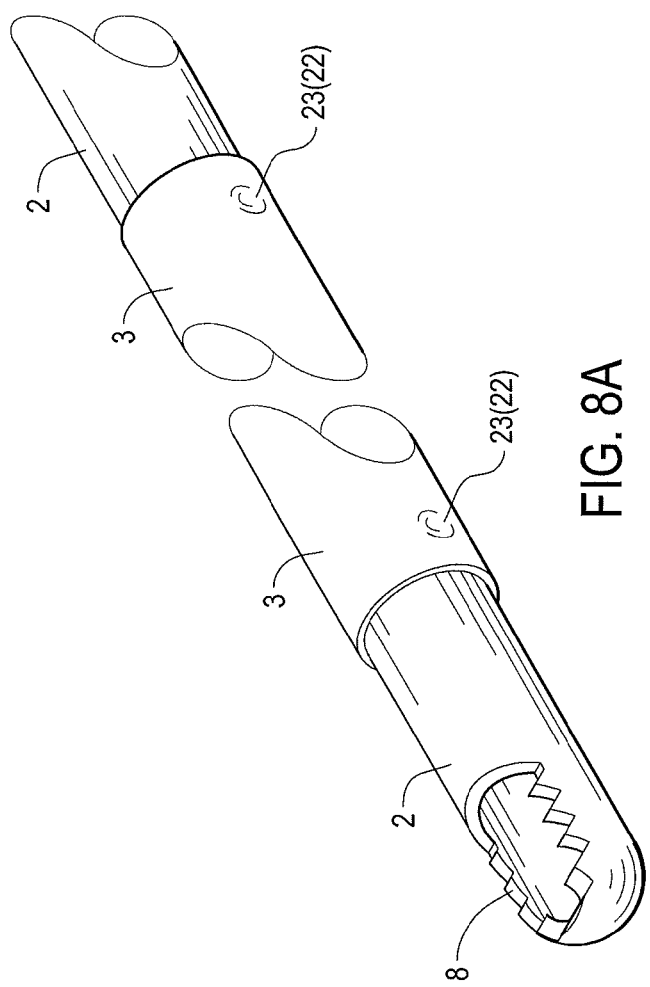
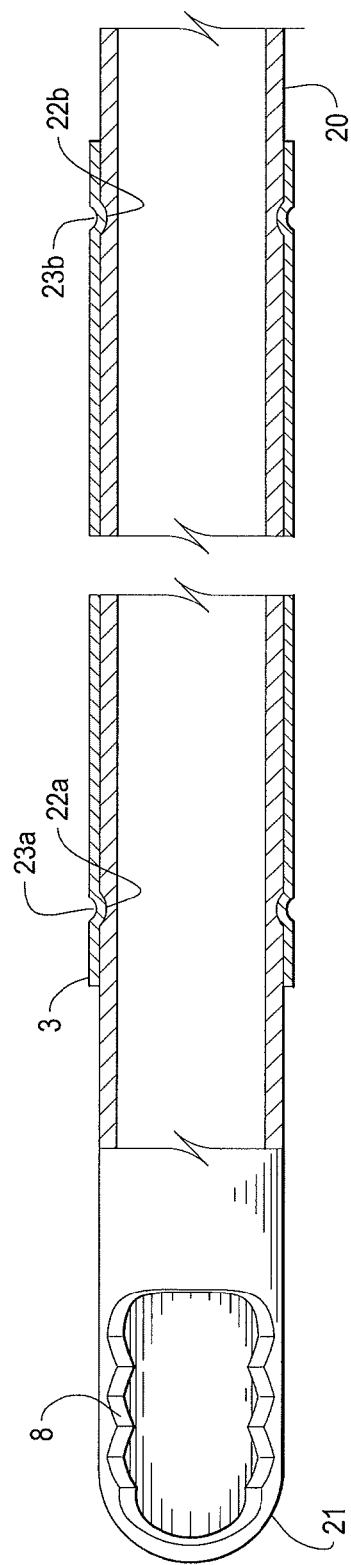
FIG. 8A
FIG. 8B

SURGICAL INSTRUMENT WITH MALLEABLE TUBING

This is a Continuation of U.S. patent application Ser. No. 13/216,714 filed Aug. 24, 2011 (now U.S. Pat. No. 9,198,685). The disclosure of the prior application is hereby incorporated by reference herein in its entirety.

BACKGROUND

This disclosure relates to surgical instruments. In particular, the disclosure relates to surgical instruments usable, for example, to shave, cut, resect, abrade and/or remove, tissue, bone and/or other bodily materials as well as applications which may use an instrument including a malleable tubing as a reinforcement to a cylindrical member. The invention is thus not limited to cutting instruments but is applicable to various surgical instruments, such as those used for suctioning, cauterizing, grasping, and/or guiding a light source, in which instruments may require different tip orientations and/or angles.

Surgical apparatus used to shave, cut, resect, abrade and/or remove tissue, bone and or other bodily materials are known as instruments for suctioning, cauterizing, grasping and guiding a light source. For example, a cutting surgical apparatus can include a cutting surface, such as a rotating blade, disposed on an elongated inner tube that is rotated within an elongated outer tube having a cutting window. The inner and outer tubes together forming a surgical cutting blade. In general, the elongated outer tube includes a distal end defining an opening or cutting window that exposes the cutting surface of the inner tube (at the distal end of the inner tube) to tissue, bone and/or any other bodily materials. A powered handpiece is used to rotate the inner tube with respect to the outer tube while an outer tube hub (connected to the proximal end of the outer tube) is rigidly fixed to the handpiece and an inner tube hub (connected to the proximal end of the inner tube) is loosely held in place by the powered handpiece and can move axially.

During surgery, it may be necessary or helpful to precisely orient a tip of the surgical cutting blade (defining the cutting surface within the cutting window) at a specific angle. Because of this requirement, it is known to provide multiple surgical cutting blades having first ends angled to different fixed degrees. Thus, depending on the needs or requirements of the surgery, a surgeon can switch between multiple different surgical cutting blades multiple times during surgery so as to precisely orient the selected surgical cutting blade in the exact location he/she is trying to reach.

Also, these surgical apparatus are also known to have bends at either, or both, the distal and proximal ends of the outer tube in order to orient the cutting window in a particular plane. Thus, the inner tube, disposed inside the outer tube, includes flexible portions adjacent the bent portions of the outer tube that allow for the inner tube to be inserted in the outer tube and rotate within the outer tube once bent.

A number of difficulties have been encountered in attempting to develop reliable flexible-shaft surgical blades that would allow the surgeon to use only one surgical cutting blade, as opposed to changing between different surgical cutting blades having different shapes and/or window orientations based on a newly desired target orientation. For example, surgical cutting blades have been developed that are initially straight and can then be bent to a desired angle. However, the drawback for this design is that once the surgical cutting blade instrument is bent, any rebend of the surgical cutting blade instrument to obtain a different angled configuration is not effective or reliable in allowing for proper rotation of the inner tube. For example, the outer tube may kink or break when rebent (or even upon its initial bending). Thus, a new surgical cutting blade must be used if a different angle configuration of the blade is required/desired. Another example involves the use of a lever arm that allows a surgeon to bend the surgical cutting blade instrument to a specific angle and hold the instrument at that angle. However, the drawback for this design is that the lever cannot be locked into place and thus requires the surgeon to continuously apply pressure to the lever in order to hold the instrument in the desired angled orientation. Additionally, typically, the bending of the instrument using the lever is limited to only one direction (typically concave) and is not bi-directional. Another problem that can occur is that the blade may not hold its bend during use if the blade is too flexible

SUMMARY

User preferences, such as those of the surgeons, as well as the demands of surgery dictate limitless requirements for the curvature of a surgical tool and for the orientation of the cutting window of the tool. Accommodating such user preferences and surgery requirements during surgical procedures requires the use of many surgical tools having different angled configurations and/or window orientations. The use of multiple surgical tools can be very costly and requires hospitals/surgeons to come equipped with a large variety of surgical tools so as to accommodate any and all needs that arise during surgery.

It would be advantageous to provide an arrangement that would allow the surgeon to utilize one surgical instrument (or blade) for all surgery requirements. In that regard, a malleable tubing is provided and disposed over the flexible region(s) of a cylindrical member. The malleable tubing allows for the flexible region(s) of the cylindrical member to be bent and retain the bent shape so as to prevent the surgical instrument from straightening during a procedure. This arrangement allows the surgeon to use one flexible member (for example, a flexible cutting blade) for many different types of surgical procedures because the flexible member can be reoriented such that the tip is angled by various different amounts and/or in various different directions. Additionally, this arrangement allows for the use of flexible members without the concern that the member will straighten (or otherwise rebend) during insertion into the body or while it is inserted into the body.

In various exemplary embodiments, a surgical instrument may include a hollow cylindrical member having a flexible region along at least a part of the hollow cylindrical member and a malleable tubing disposed over at least an outer surface of the flexible region of the hollow cylindrical member. The flexible region and the malleable tubing disposed over the flexible region may be bent multiple times. The malleable tubing may maintain a bent orientation until the malleable tubing is re-bent by a user.

In some embodiments, the surgical instrument may further include an inner hollow cylindrical member disposed within the hollow cylindrical member and having a flexible region along at least a part of the inner hollow cylindrical member. At least a part of the flexible region of the hollow cylindrical member may overlap at least a part of the flexible region of the inner hollow cylindrical member.

In some embodiments, the flexible region of the hollow cylindrical member is formed by at least one helical cut made in the hollow cylindrical member. The at least one helical cut extends around a circumference of the hollow cylindrical member for an entire length of the flexible region.

In some embodiments, the malleable tubing is made of an anodized annealed metal or an annealed metal. In some embodiments, the metal is aluminum.

In some embodiments, the malleable tubing is made of a metal such as, for example, aluminum or copper.

In some embodiments, the metal is an annealed metal.

In some embodiments, the flexible region of the hollow cylindrical member is formed by slits made in the hollow cylindrical member. Each of the slits extends partially around a circumference of the hollow cylindrical member without extending entirely around the circumference of the hollow cylindrical member.

It is preferable that the hollow cylindrical member has a hoop strength sufficient to prevent the malleable tubing from flattening when the malleable tubing and the hollow cylindrical member are bent.

In some embodiments, the surgical instrument may further include connections between the hollow cylindrical member and the malleable tubing to prevent the malleable tubing from moving longitudinally relative to the hollow cylindrical member. The connections are located distally and proximally of the flexible region of the hollow cylindrical member.

In some embodiments, for example, the connections include first and second dimples. The first dimples are formed in the hollow cylindrical member and extend radially inward. The second dimples are formed in the malleable tubing and extend radially inward toward the hollow cylindrical member. The second dimples extend into the first dimples to fixedly attach the malleable tubing to the hollow cylindrical member.

In some embodiments, for example, the connections include first and second radially protruding collars. The first radially protruding collar is disposed on the hollow cylindrical member distally of the flexible region of the hollow cylindrical member. The second radially protruding collar is disposed on the hollow cylindrical member proximally of the flexible region of the hollow cylindrical member. The malleable tubing is located between the first and second radially protruding collars such that the first and second radially protruding collars abut the malleable tubing and restrict axial movement of the malleable tubing with respect to the hollow cylindrical member.

In some embodiments, for example, the connections include holes extending through the malleable tubing as well as welds extending through the holes and attached to the hollow cylindrical member.

In some embodiments, for example, the connections include a shrink-wrap covering disposed over at least the malleable tubing and portions of the hollow cylindrical member located distally and proximally of the malleable tubing. The shrink-wrap covering restricts axial and rotational movement of the malleable tubing with respect to the hollow cylindrical member.

In some embodiments, for example, the connections include raised knurled portions of the hollow cylindrical member. The malleable tubing is friction fitted to the raised knurled portions to restrict axial and rotational movement of the malleable tubing with respect to the hollow cylindrical member.

In some embodiments, the hollow cylindrical member is a helical spring.

In some embodiments, the hollow cylindrical member and the inner hollow cylindrical member, excluding the flexible regions, are rigid conduits.

In some embodiments, the hollow cylindrical member includes a cutting window at its distal end and the inner hollow cylindrical member is rotatable within the hollow cylindrical member and includes a cutting window at its distal end. The cutting windows of the hollow cylindrical member and the inner hollow cylindrical member are aligned with each other and function to cut and remove tissue when the inner hollow cylindrical member is rotated while suctioning through the inner hollow cylindrical member.

In some embodiments, the hollow cylindrical member is a multifilar wire coil having one or more layers.

BRIEF DESCRIPTION OF THE DRAWINGS

Various exemplary embodiments of the disclosed surgical instrument will be described in detail with reference to the following drawings in which:

FIGS. 2A-B illustrate a perspective view of an exemplary embodiment of the surgical instrument when bent once (FIG. 2A) or more than once (FIG. 2B);

FIG. 3 illustrates a perspective view of an exemplary embodiment of a hollow cylindrical member of the surgical instrument with a helical cut in the hollow cylindrical member;

FIG. 4 illustrates a perspective view of an exemplary embodiment of a hollow cylindrical member of the surgical instrument with multiple slits in the hollow cylindrical member;

FIG. 8A illustrates a perspective view of an exemplary embodiment of the surgical instrument including dimples for connecting the hollow cylindrical member and the malleable tubing; FIG. 8B illustrates a cross-sectional view of FIG. 8A;

DETAILED DESCRIPTION OF EMBODIMENTS

Figure 1:
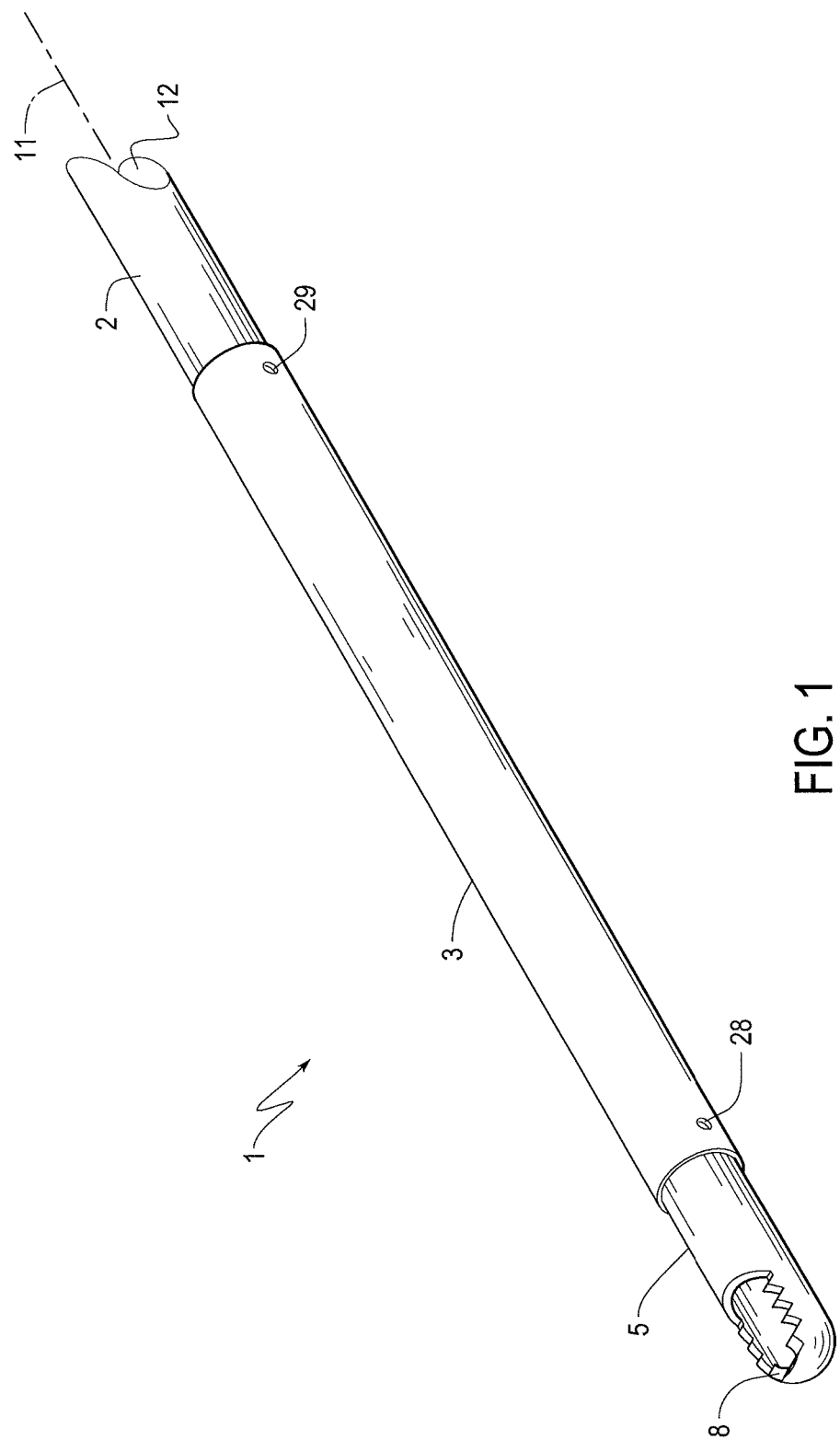
FIG. 1 illustrates a perspective view of an exemplary embodiment of the surgical instrument in accordance with the present disclosure.
Figure 5:
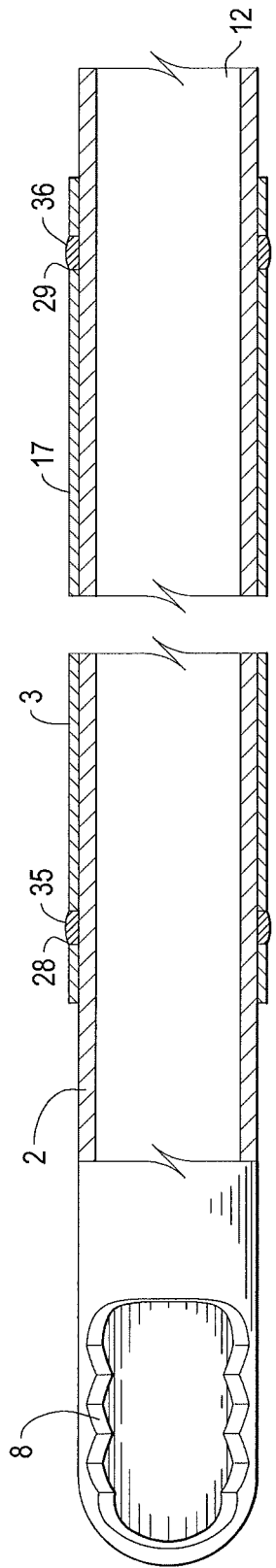
FIG. 5 illustrates a cross-sectional view of the exemplary embodiment of FIG. 1.

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor. Moreover, the invention is not limited to surgical cutting instruments. The invention is applicable to any surgical device in which it is desired to provide a bendable flexible member (such as, for example, a hollow tube) that can be bent into multiple, different configurations, stay in that configuration during use, and then can be rebent into a different configuration.

FIGS. 1-6 illustrate views of an exemplary embodiment of a surgical instrument 1 in accordance with aspects of the invention. The surgical instrument 1 includes a hollow cylindrical member 2 and a malleable tubing 3 disposed over an outer surface 5 of the hollow cylindrical member 2. The malleable tubing 3 is tightly fitted around the hollow cylindrical member 2 such that movement of the malleable tubing 3 in the axial direction with respect to the hollow cylindrical member 2 is prevented. Thus, the malleable tubing 3 has a slightly larger diameter than the hollow cylindrical member 2, allowing for insertion of the hollow cylindrical member 2 within the malleable tubing 3. However, it should be appreciated that the hollow cylindrical member 2 and malleable tubing will be pre-assembled prior to delivery to the customer. Thus, a customer will most likely not be inserting the hollow cylindrical member 2 into the malleable tubing 3. Instead, the customer will merely be utilizing the flexibility imparted by a flexible region 4 of the hollow cylindrical member 2 (FIGS. 3 and 4) and the malleable tubing 3 to flex a portion of the surgical instrument 1 so as to orient a cutting window 8 of the hollow cylindrical member 2, for example, in a different plane than previously disposed.

FIG. 2A illustrates the flexibility of the flexible region 4 of the hollow cylindrical member 2 and the malleable tubing 3 by illustrating a first bend 6. In order to obtain the first bend 6, a user must apply a minimal amount of pressure to the malleable tubing 3 surrounding the flexible region 4 of the hollow cylindrical member 2. Once the malleable tubing 3 surrounding the flexible region 4 of the hollow cylindrical member 2 has been bent, the malleable tubing 3 allows for the surgical instrument 1 to maintain (hold) the bend 6 until the user re-bends or straightens the malleable tubing 3. Thus, the malleable tubing 3 and the hollow cylindrical member 2 can be bent multiple times at the same location. Additionally, as illustrated in FIG. 2B, the first bend 6 can be maintained even when pressure is reapplied to the malleable tubing 3 in order to result in a second bend 7 distal (or proximal) of the first bend 6.

The malleable tubing 3 is formed from a metal that allows for flexibility while retaining a bent orientation upon release of bending pressure. The metal can be any metal that allows the user to apply pressure to the malleable tubing 3 covering a portion of the flexible region 4 of the hollow cylindrical member 2, or covering a portion of the flexible region 4 of the hollow cylindrical member 2 and a flexible region 14 of an inner hollow cylindrical member 13, to flex and form a bend while still retaining the bend upon release of the pressure. For example, the malleable tubing can be any malleable metal such as, for example, annealed copper (with coating or treatment to make it biocompatible), anodized annealed aluminum, annealed stainless steel, nitinol, and brass.

The hollow cylindrical member 2 has a hoop strength sufficient to prevent the malleable tubing 3 from flattening when the malleable tubing 3 and the hollow cylindrical member 2 are bent. For example, the hollow cylindrical member can be made of stainless steel or any other suitable material that will allow for the flexibility of the flexible region 4 while at the same time preventing flattening by having a sufficient hoop strength. Although the malleable tubing 3 would tend to kink when bent if it is not disposed over the hollow cylindrical member 2, the hollow cylindrical member 2 prevents the malleable tubing from kinking or flattening when bent by providing sufficient hoop strength to the overall device. Thus, disposing the malleable tubing 3 over the hollow cylindrical member 2 results in a device having a combination of qualities not present individually in either the tubing 3 or the cylindrical member 2. In particular, the overall device can be bent into various configurations without kinking or flattening and it can stay in its bent configuration (i.e., it is sufficiently rigid after it has been bent) until the user rebends the device.

FIGS. 3 and 4 illustrate at least one flexible region 4 of the hollow cylindrical member 2. However, the hollow cylindrical member 2 is not limited to a single flexible region and can have multiple flexible regions. Other than the flexible region(s) 4, the remainder of the hollow cylindrical member 2 is a rigid conduit 10. The rigid conduit 10 of the hollow cylindrical member 2 may include at least a portion of the hollow cylindrical member 2 including the cutting window 8 at the distal end 21 of the hollow cylindrical member 2 and may also include a portion of the hollow cylindrical member 2 near the proximal end 20 of the hollow cylindrical member 2. The flexible region 4 of the hollow cylindrical member 2 is located near the distal end 21 of the hollow cylindrical member 2 and extends for a distance along the length of the hollow cylindrical member 2. However, the invention is not limited to the configuration of the exemplary embodiments of FIGS. 3 and 4. The flexible region(s) 4 of the hollow cylindrical member 2 can be located along any portion or even along almost the entire length of the hollow cylindrical member 2. Additionally, the flexible region(s) 4 of the hollow cylindrical member 2 can be located at multiple, different locations along the hollow cylindrical member 2.

As illustrated in FIG. 3, the flexible region 4 of the hollow cylindrical member 2 can be formed by a helical cut 15 made in the hollow cylindrical member 2 such that the helical cut 15 extends around a circumference of the hollow cylindrical member 2 for an entire length of the flexible region 4. The helical cut 15 can extend completely through to the interior of the hollow cylindrical member 2 but is not limited to this arrangement. The helical cut 15 allows for the formation of the flexible region 4, which is easily flexed about the longitudinal axis 11 of the surgical instrument 1 in any direction orthogonal to the longitudinal axis 11. Additionally, the invention is not limited to the configuration of a single helical cut. The flexible region 4 may be made of multiple helical cuts. The hollow cylindrical member 2 can also include multiple, different locations of flexible regions. Thus, the different flexible regions will each be formed of a different or multiple helical cut(s). A helical cut preferably is used with an aluminum tube that is fixed at both ends of the flex to maintain planarity of the flexible tube. Conversely, slits in the flexible tube preferably are used with an aluminum tube that is fixed at only one end.

As illustrated in FIG. 4, the flexible region 4 of the hollow cylindrical member 2 can be formed by slits 19 made in the hollow cylindrical member 2. The slits 19 extend partially around a circumference of the hollow cylindrical member 2 without extending entirely around the circumference of the hollow cylindrical member 2. The slits 19 can extend completely through to the interior of the hollow cylindrical member 2 but are not limited to this arrangement. The slits 19 allow for the formation of the flexible region 4, which is capable of flexing about the longitudinal axis 11 of the surgical instrument 1, though not in as many directions as the flexible region 4 formed by the helical cut 15. Additionally, the invention is not limited to this configuration of slits. The hollow cylindrical member 2 can include multiple, different locations of flexible regions. Thus, the different flexible regions may each be formed of a different set of slits. When adjacent slits 19 are all the same (as shown in FIG. 4), the hollow cylindrical member 2 can bend in one plane. If the slits 19 extend through the tube in different radial directions, the hollow cylindrical member 2 can bend in as many directions as there are radially extending slit variations.

Figure 6:
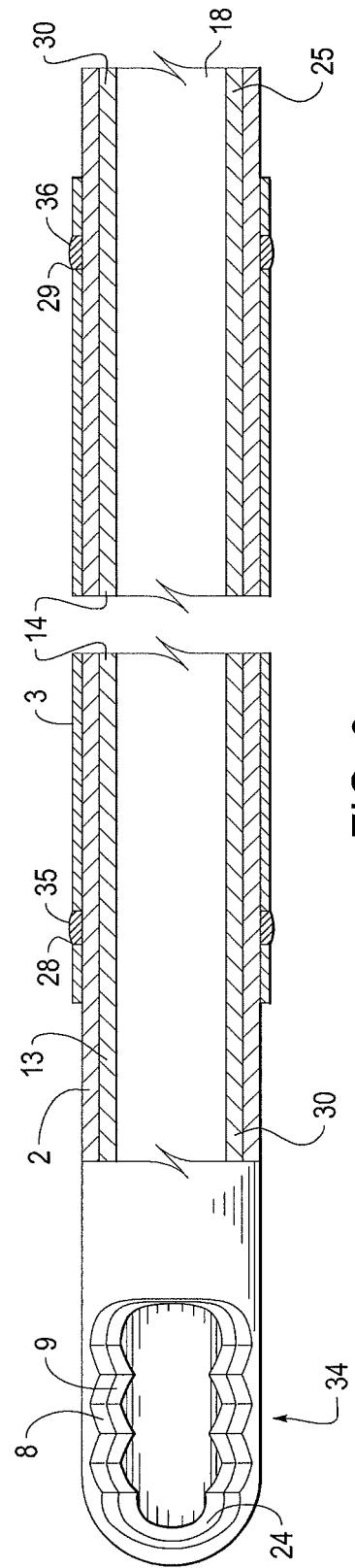
FIG. 6 illustrates a cross-sectional view of the exemplary embodiment of FIG. 1 including an inner hollow cylindrical member disposed within the hollow cylindrical member.

FIG. 6 illustrates a cross-sectional view of an exemplary embodiment of the surgical instrument 1 in accordance with aspects of the invention. The surgical instrument 1 incorporates the hollow cylindrical member 2, malleable tubing 3, and an inner hollow cylindrical member 13. In this exemplary embodiment, the inner hollow cylindrical member 13 is inserted into a fluid passage 12 of the hollow cylindrical member 2 (FIG. 1) formed within the hollow cylindrical member 2 so that the inner hollow cylindrical member 13 is co-axially disposed within the hollow cylindrical member 2. The hollow cylindrical member 2 has a larger inner diameter than the outer diameter of the inner hollow cylindrical member 13, thus allowing for insertion of the inner hollow cylindrical member 13 within the hollow cylindrical member 2. However, it should be appreciated that the inner hollow cylindrical member 13 and hollow cylindrical member 2 will be pre-assembled prior to delivery to the customer. Thus, a customer will most likely not be inserting the inner hollow cylindrical member 13 into the hollow cylindrical member 2. Instead, the customer will merely be utilizing the flexibility imparted by the flexible region 4 of the hollow cylindrical member 2, a flexible region 14 of the inner hollow cylindrical member 2 and the malleable tubing 3 to flex a portion of the surgical instrument 1 so as to orient cutting window 8 of the hollow cylindrical member 13 and a cutting surface 9 of the inner hollow cylindrical member 13, for example, in a different plane than previously disposed.

The inner hollow cylindrical member 13 includes a fluid/bodily materials removal passage 18 that extends the length of the inner hollow cylindrical member 13. The inner hollow cylindrical member 13 also includes the cutting surface 9 at the distal end 24 of the inner hollow cylindrical member 13. The inner hollow cylindrical member 13 is co-axially disposed within the hollow cylindrical member 2 such that the cutting surface 9 is exposed at the cutting window 8. The cutting surface 9 disposed within the cutting window 8 forms a cutting instrument 34, which cuts by rotating the inner hollow cylindrical member 13 within the hollow cylindrical member 2. The surgical instrument 1 with the cutting instrument 34 at its distal end is used to cut, shave, resect, and/or abrade tissue, bone, and/or other bodily materials. The surgical cutting instrument 34 is to be used in a powered surgical tool system such as disclosed in U.S. Pat. No. 7,247,161, the disclosure of which is incorporated herein by reference in its entirety. The instrument of FIG. 6 is a surgical shaver or microdebrider, for use in endoscopic surgical procedures, that drives an elongated rotatable surgical instrument and aspirates material from a surgical work site. In operation, a surgeon grasps an elongated body of a handpiece in a manner similar to gripping a writing apparatus, such as a pen or pencil. While gripping the body of the handpiece in this manner, the surgeon is able to direct the distal end of the shaver blade assembly to the bodily material to be cut. The surgeon can manipulate the device such that the cutting window 8 is disposed adjacent to the tissue to be cut, and then the surgeon causes the inner member 13 to rotate while aspirating fluid through passage 18. Liquid also can be supplied to the site through passage 12 during the surgical procedure. However, the surgical instrument 1 is not limited to endoscopic procedures but can, additionally, be used in non-endoscopic procedures where such a surgical instrument 1 configuration is desirable.

As discussed above with respect to the hollow cylindrical member 2, the inner hollow cylindrical member 13 includes at least one flexible region 14. However, the inner hollow cylindrical member 13 is not limited to a single flexible region and can have multiple flexible regions. Other than the flexible region 14, the remainder of the inner hollow cylindrical member 13 is a rigid conduit 30. The rigid conduit 30 of the inner hollow cylindrical member 13 may include at least a portion of the inner hollow cylindrical member 13 including the cutting surface 9 at the distal end 24 of the inner hollow cylindrical member 13 and may also include a portion of the inner hollow cylindrical member 13 near the proximal end 25 of the inner hollow cylindrical member 13. The flexible region 14 of the inner hollow cylindrical member 13 is located near the distal end 24 of the inner hollow cylindrical member 13 and extends for a distance along the length of the inner hollow cylindrical member 13. However, the invention is not limited to the configuration of the exemplary embodiments. The flexible region 14 of the inner hollow cylindrical member 13 can be located along any portion or even along almost the entire length of the inner hollow cylindrical member 13. Additionally, the flexible region(s) 14 of the inner hollow cylindrical member 13 can be located at multiple, different locations along the inner hollow cylindrical member 13.

Similar to the flexible region 4 of the hollow cylindrical member 2 illustrated in FIG. 3, the flexible region 14 of the inner hollow cylindrical member 13 can be formed by a helical cut (not shown—refer to FIG. 3 of the hollow cylindrical member 2) made in the inner hollow cylindrical member 13 such that the helical cut extends around a circumference of the inner hollow cylindrical member 13 for an entire length of the flexible region 14. The helical cut can extend completely through to the interior of the inner hollow cylindrical member 13 but is not limited to this arrangement. The helical cut allows for the formation of the flexible region 14, which is easily flexed about the longitudinal axis 11 of the surgical instrument 1. Additionally, the invention is not limited to the configuration of a single helical cut. The flexible region 14 may be made of multiple helical cuts. The inner hollow cylindrical member 13 can also include multiple, different locations of flexible regions 14. Thus, the different flexible regions will each be formed of a single or multiple helical cut(s).

Various structures can be used to form the flexible inner hollow cylindrical member 13. As shown, for example, in U.S. Pat. No. 5,707,350, the disclosure of which is incorporated herein by reference in its entirety, a rigid tube can be laser cut to form openings in it to render it flexible, and then the laser cut tubing can be wrapped with a layer of pliable material to hold it together. According to another example, shown in U.S. Pat. No. 4,646,738, the disclosure of which is incorporate herein by reference in its entirety, two or more flexible strips of metal are wound into overlapping coils to form the flexible portion of the inner hollow cylindrical member 13. Similar techniques can be used to form the hollow cylindrical member 2.

The flexible region 14 of the inner hollow cylindrical member 13 can extend along a greater length of the inner hollow cylindrical member 13 than the flexible region 4 of the hollow cylindrical member 2. In the illustrated embodiment of FIG. 6, the flexible region 4 of the hollow cylindrical member 2 starts at a position close to the cutting window 8 and extends for a distance, and the flexible region 14 of the inner hollow cylindrical member 13 starts at a position close to the cutting surface 9 and extends for a greater distance. However, at least a part of the flexible region 4 of the hollow cylindrical member 2 overlaps at least a part of the flexible region 14 of the inner hollow cylindrical member 13.

The flexible regions 4, 14 are radially, symmetrically bendable about the longitudinal axis 11 of the surgical instrument 1. That is, the flexible regions 4, 14 can be bent in any direction (up, down, left, right, and all directions in between). However, in one embodiment, for example, the flexible region 4 of the hollow cylindrical member 2 assumes a substantially straight orientation when the malleable tubing 3 is disposed over the hollow cylindrical member 2 (FIG. 1). In another embodiment, for example, the flexible region 4 assumes a bent orientation to form a first bend 6 (FIG. 2A). In yet another embodiment, for example, the same flexible region 4, as FIG. 2A, assumes a second bent orientation to form a second bend 7 (FIG. 2B).

In order to fixedly connect the malleable tubing 3 to the hollow cylindrical member 2, connections are formed between the hollow cylindrical member 2 and the malleable tubing 3 that prevent the malleable tubing 3 from moving longitudinally or rotationally, in some embodiments, relative to the hollow cylindrical member 2. The connections are located distally and proximally of the flexible region 4 of the hollow cylindrical member 2. Additionally, in some embodiments, the flexible region 4 of the hollow cylindrical member 2 has a larger outer diameter than the adjacent rigid conduit 10 portion. Thus, the malleable tubing 3 can be manually crimped/swaged down onto the smaller outer diameter rigid conduit 10 portion, fixing the malleable tubing 3 in place. Additionally, in some embodiments, the malleable tubing 3 is bonded to the hollow cylindrical member 2 with an adhesive, such as, for example, a cyanoacrylate or an epoxy.

FIG. 1 illustrates a first example of connections that fixedly connect the malleable tubing 3 to the hollow cylindrical member 2. A first hole 28 in the malleable tubing 3 is located between the flexible region 4 of the hollow cylindrical member 2 and the cutting window 8 of the hollow cylindrical member 2. A second hole 29 in the malleable tubing 3 is located proximally of the flexible region 4 and thus, is located between the flexible region 4 of the hollow cylindrical member 2 and the proximal end 20 of the hollow cylindrical member 2. The holes 28, 29 extend completely through the malleable tubing 3 to the outer surface 5 of the hollow cylindrical member 2. The holes are then welded such that a first weld 35 extends through the first hole 28 and a second weld 36 extends through the second hole 29. The first weld 35 attaches the hollow cylindrical member 2 to the malleable tubing 3 at the distal end 21 of the hollow cylindrical member 2. The second weld 36 attaches the hollow cylindrical member 2 to the malleable tubing 3 at the proximal end 20 of the hollow cylindrical member 2. The invention is not restricted to the configuration as depicted in FIG. 1. For example, the hole 28 with weld 35 extending through can be located at any point between the flexible region 4 of the hollow cylindrical member 2 and the cutting window 8 of the hollow cylindrical member 2. Also, the hole 29 with weld 36 extending through can be located at any point between the flexible region 4 of the hollow cylindrical member 2 and the proximal end 20 of the hollow cylindrical member 2.

Figure 7:
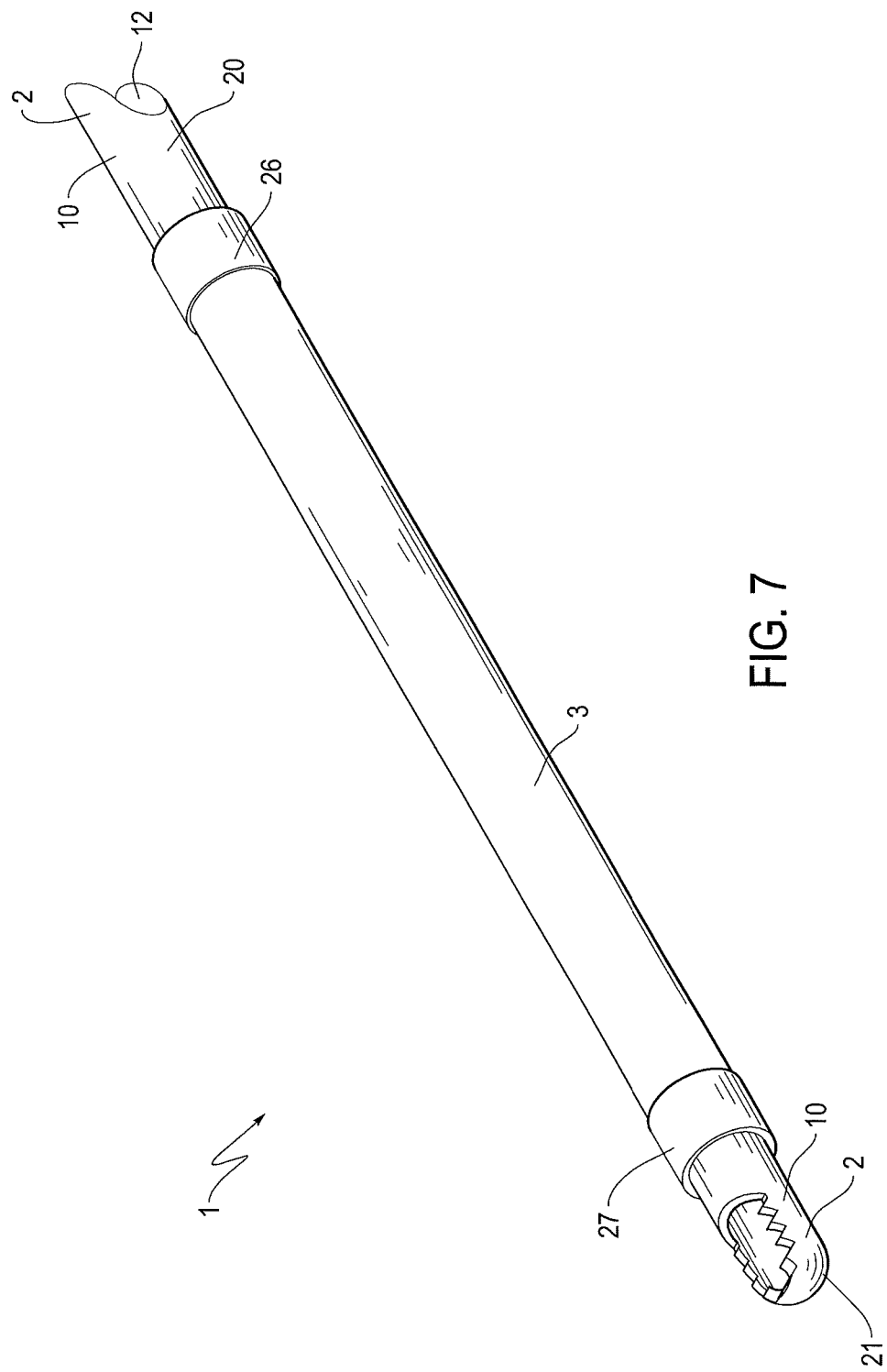
FIG. 7 illustrates a perspective view of an exemplary embodiment of the surgical instrument including collars for connecting the hollow cylindrical member and the malleable tubing.

FIG. 7 illustrates another example of connections including a first radially protruding collar 26 and a second radially protruding collar 27 that fixedly connect the malleable tubing 3 to the hollow cylindrical member 2. The first radially protruding collar 26 extends along the outer surface 5 of the hollow cylindrical member 2 and is located proximally of the flexible region 4 of the hollow cylindrical member 2. The second radially protruding collar 27 extends along the outer surface 5 of the hollow cylindrical member 2 and is located distally of the flexible region 4 of the hollow cylindrical member 2. The malleable tubing 3 is located between the first radially protruding collar 26 and the second radially protruding collar 27 such that the collars 26, 27 abut the malleable tubing 3 and restrict longitudinal movement of the malleable tubing 3 with respect to the hollow cylindrical member 2. The collars 26, 27 are not limited to those depicted in FIG. 7. For example, the collars 26, 27 can extend along the entire length of the rigid conduit 10 of the hollow cylindrical member 2 or just a portion of the hollow cylindrical member, as long as the collars 26, 27 abut the malleable tubing 3.

FIGS. 8A-B illustrate another example of connections including first dimples 22 and second dimples 23 that fixedly connect the malleable tubing 3 to the hollow cylindrical member 2. The first dimples 22 include a first distal dimple 22a and a first proximal dimple 22b. The first distal dimple 22a is formed distally of the flexible region 4 of the hollow cylindrical member 2 in the outer surface 5 of the hollow cylindrical member 2 and extends radially inward. The first proximal dimple 22b is formed proximally of the flexible region 4 of the hollow cylindrical member 2 in the outer surface 5 of the hollow cylindrical member 2 and extends radially inward. The second dimples 23 include a second distal dimple 23a and a second proximal dimple 23b. The second distal dimple 23a is formed distally of the flexible region 4 of the hollow cylindrical member 2 in the malleable tubing 3 and extends radially inward toward the hollow cylindrical member 2. The second proximal dimple 23b is formed proximally of the flexible region 4 of the hollow cylindrical member 2 in the malleable tubing 3 and extends radially inward toward the hollow cylindrical member 2. The second distal dimple 23a extends into the first distal dimple 22a and the second proximal dimple 23b extends into the first proximal dimple 22b to fixedly attach the malleable tubing 3 to the hollow cylindrical member 2. However, the dimples are not limited to the configuration depicted in FIG. 8. For example, the malleable tubing 3 and/or hollow cylindrical member 2 may include more than one proximal and/or distal dimple. The dimples are easy to form and do not increase the overall diameter of the surgical instrument. Additionally, the dimples may extend radially around the tube/members from 0-360° of the tube's/member's circumference, to form a crimped groove, or "corset."

Figure 9:
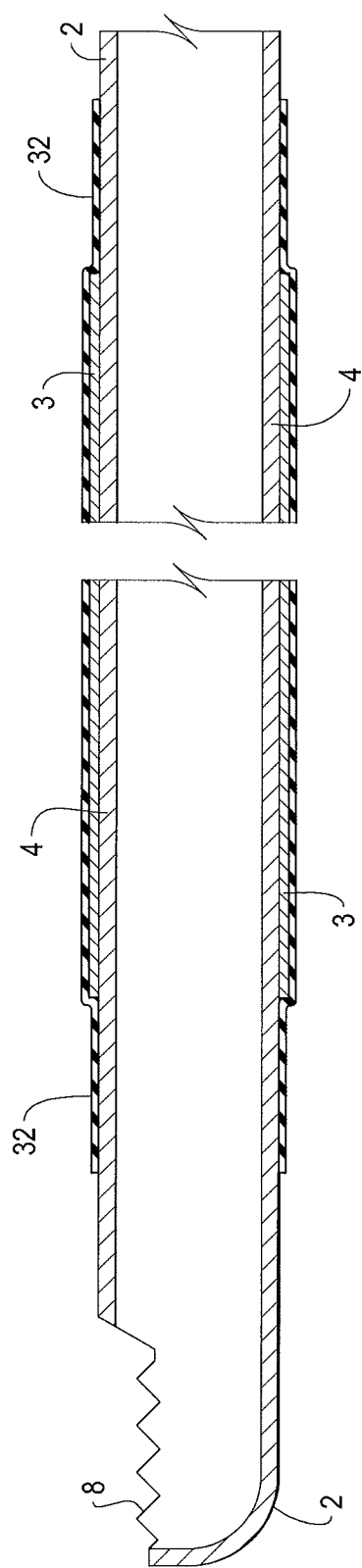
FIG. 9 illustrates a cross-sectional view of an exemplary embodiment of the surgical instrument including shrink wrap covering for connecting the hollow cylindrical member and the malleable tubing.

FIG. 9 illustrates another example of connections including a shrink-wrap covering 32 that fixedly connects the malleable tubing 3 to the hollow cylindrical member 2. The shrink-wrap covering 32 is disposed over the circumference of at least the malleable tubing 3 and portions of the hollow cylindrical member 2 located distally and proximally of the malleable tubing 3 or over substantially the entire hollow cylindrical member 2 excluding the portion of the hollow cylindrical member 2 including the cutting window 8. The shrink-wrap covering 32 restricts both axial and rotational movement of the malleable tubing 3 with respect to the hollow cylindrical member 2.

Figure 10:
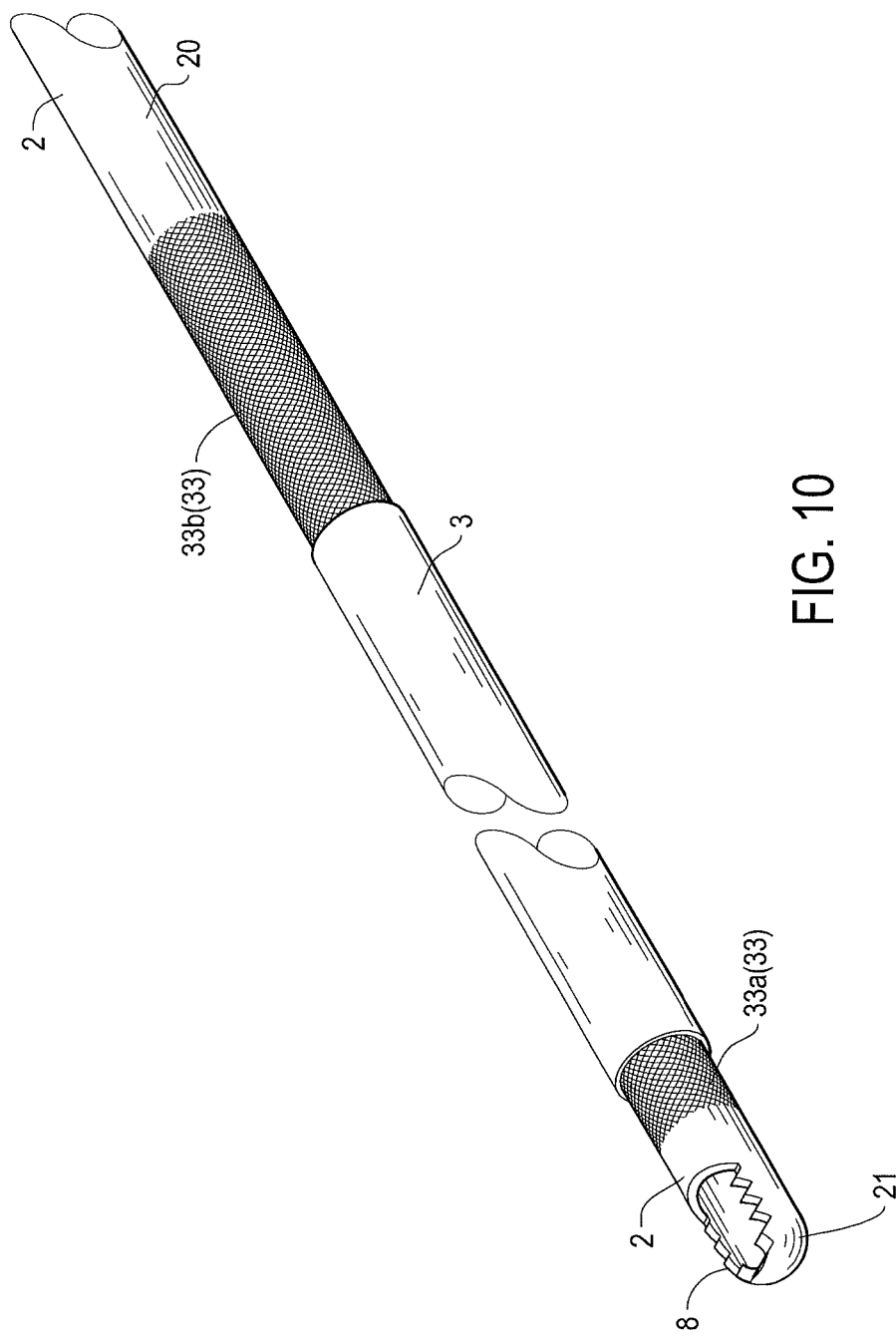
FIG. 10 illustrates a perspective view of an exemplary embodiment of the surgical instrument including raised knurled portions for connecting the hollow cylindrical member and the malleable tubing.

FIG. 10 illustrates another example of connections including raised knurled portions 33 that frictionally and fixedly connect the malleable tubing 3 to the hollow cylindrical member 2. The raised knurled portions 33 are formed on the hollow cylindrical member 2. The malleable tubing 3 is friction fitted to the raised knurled portions 33 to restrict axial and rotational movement of the malleable tubing 3 with respect to the hollow cylindrical member 2.

The raised knurled portions 33 include, for example, a first raised knurled portion 33a located distally of the flexible region 4 of the hollow cylindrical member 2 and a second raised knurled portion 33b located proximally of the flexible region 4 of the hollow cylindrical member 2. The first raised knurled portion 33a extends completely beneath the malleable tubing 3 or extends for a certain distance beneath the malleable tubing 3 and for a distance distally of an end of the malleable tubing 3. The second raised knurled portion 33b extends completely beneath the malleable tubing 3 or extends for a certain distance beneath the malleable tubing 3 and for a distance proximally of an end of the malleable tubing 3. However, the invention is not limited to this configuration. For example, excluding the flexible region 4 of the hollow cylindrical member 2, the raised knurled portions 33 can cover the remaining rigid conduit 10 of the hollow cylindrical member 2 such that the malleable tubing is friction fitted over the hollow cylindrical tubing 2. Additionally, the raised knurled portions 33 may extend around a portion of the entire circumference of the hollow cylindrical member 2 or may only partially extend around the circumference of the hollow cylindrical member 2 as long as the malleable tubing is prevented from axial and rotational movement.

Figure 11:
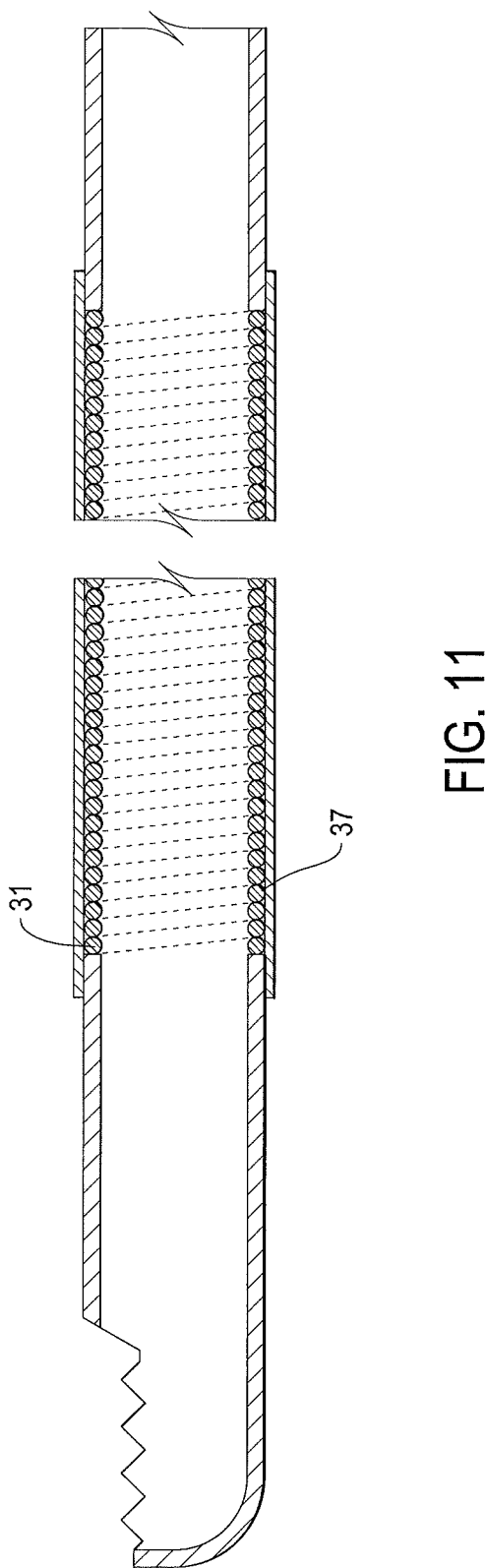
FIG. 11 illustrates a cross-sectional view of an exemplary embodiment of the surgical instrument in accordance with the present disclosure.

FIG. 11 illustrates another exemplary embodiment of the present invention. In this embodiment, the hollow cylindrical member 2 is a helical spring 31. Thus, the surgical instrument 1 incorporates a helical spring 31 and a malleable tubing 3 disposed over an outer surface 37 of the helical spring 31. The malleable tubing 3 is tightly fitted around the helical spring 31 such that movement of the malleable tubing 3 in the axial direction with respect to the helical spring 31 is prevented. Thus, the malleable tubing 3 has a slightly larger diameter than the helical spring 31, allowing for insertion of the helical spring 31 within the malleable tubing 3. However, it should be appreciated that the helical spring 31 and malleable tubing will be pre-assembled prior to delivery to the customer. Thus, a customer will most likely not be inserting the helical spring 31 into the malleable tubing 3. Instead, the customer will merely be utilizing the flexibility imparted by the flexibility of the helical spring 31 and the malleable tubing 3 to flex a portion of the surgical instrument 1 so as to orient an end of the helical spring 31/malleable tubing 3, for example, in a different plane than previously disposed. However, the invention is not limited to either a hollow cylindrical member or helical spring. For example, the hollow cylindrical member or helical spring can both be replaced with any cylindrical member that would benefit from being bent and would allow for a flexible region over which the malleable tubing 3 can be disposed.

Figure 12A:
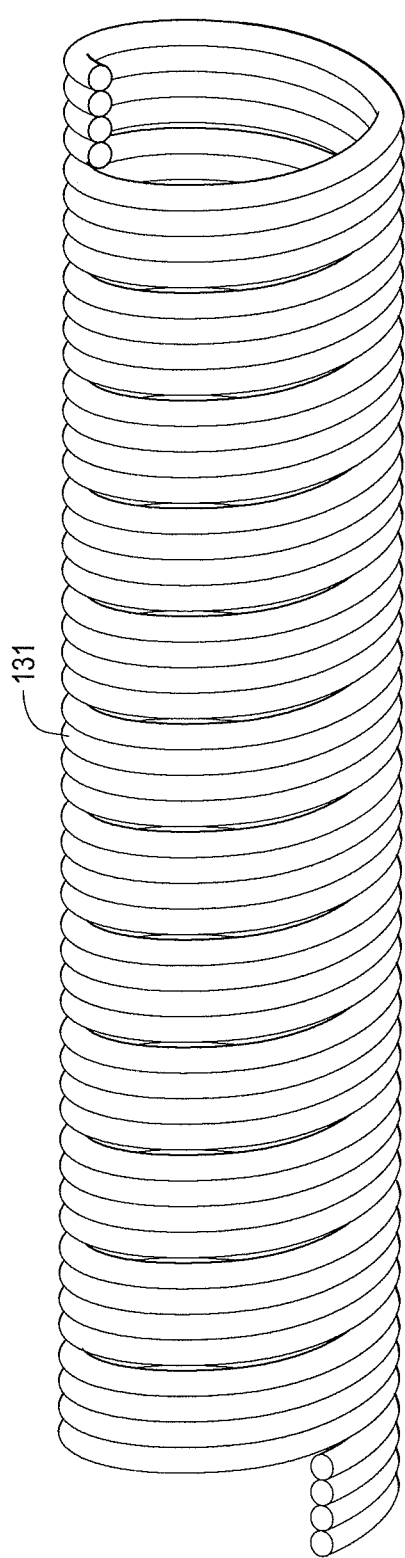
FIGS. 12A-B are side views of an exemplary embodiment of the surgical instrument in accordance with the present disclosure illustrating a multifilar and a multilayer wire coil, respectively.
Figure 12B:
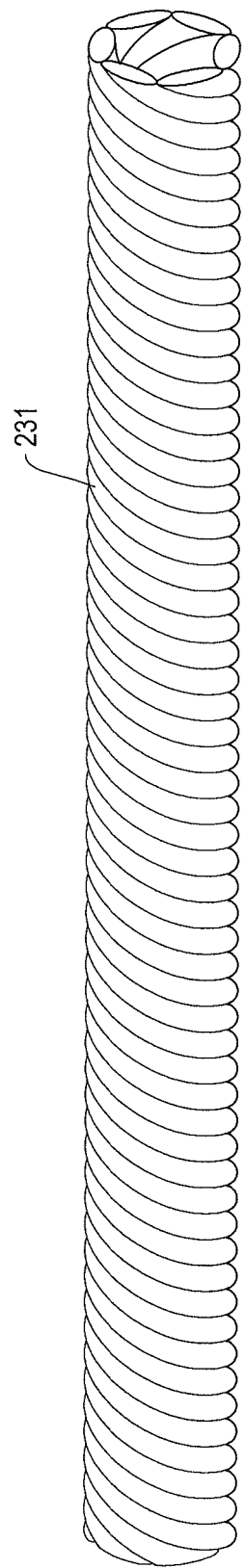

FIGS. 12A-B illustrate further exemplary embodiments of the present invention. In these embodiments, helical spring 31 can be a multifilar 131 (FIG. 12A) or multilayer (FIG. 12B) wire coil 231. A multifilar wire coil 131 is a winding of more than one wire in a layer; whereas, a multilayer wire coil 231 is a winding having more than one radial layer, usually wound in opposite directions. These wire coils are effectively modified flexible springs (also known as "torque shafts").

Figure 13:
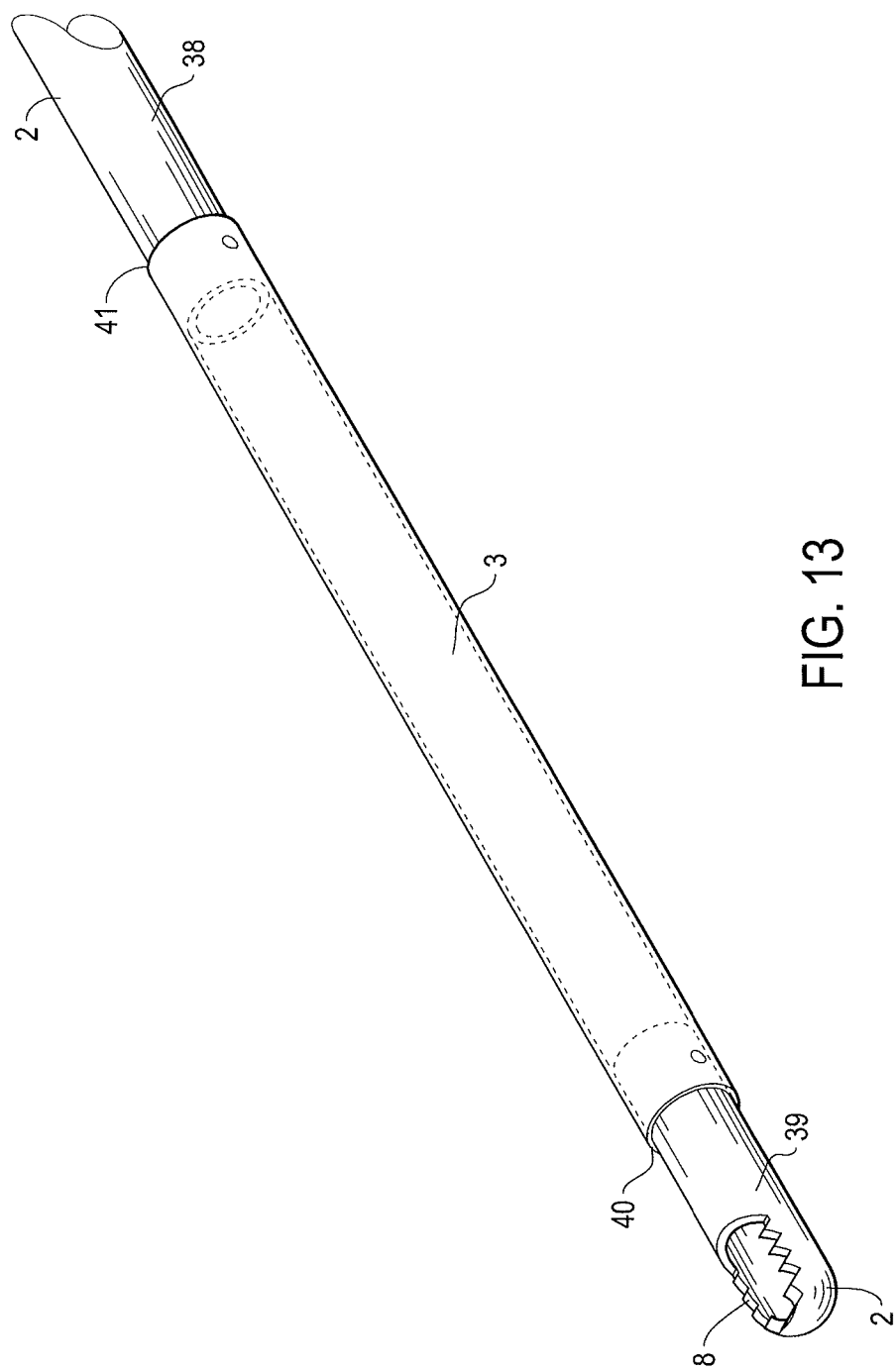
FIG. 13 is a perspective view of an exemplary embodiment of the surgical instrument having a three-piece construction in accordance with the present disclosure.

FIG. 13 illustrates another exemplary embodiment of the present invention. In this embodiment, the surgical instrument 1 is formed from three pieces. The three-piece design includes a proximal portion 38 of the hollow cylindrical member 2, malleable tubing 3, and a distal portion 39 of the hollow cylindrical member 2. The distal portion 39 of the hollow cylindrical member is attached to a first end 40 of the malleable tubing 3 and the proximal portion 38 of the hollow cylindrical member 2 is attached to a second end 41 of the malleable tubing 3. Thus, the malleable tubing 3 extends between the proximal portion 38 and the distal portion 39 of the hollow cylindrical member 2. The malleable tubing is flexible about the longitudinal axis 11 of the surgical instrument 1. However, once the malleable tubing 3 has been bent, the malleable tubing 3 allows for the surgical instrument 1 to maintain the bend until the user re-bends or straightens the malleable tubing 3. Thus, the malleable tubing can be bent multiple times at the same location.

The malleable tubing 3 can be fixedly attached to the distal portion 39 and proximal portion 38 of the hollow cylindrical member 2 by, for example, a first hole 28 in the malleable tubing 3 located at the first end 40 of the malleable tubing 3 and a second hole 29 in the malleable tubing 3 located at the second end 41 of the malleable tubing. The holes 28, 29 extend completely through the malleable tubing 3 to the outer surface 5 of the hollow cylindrical member 2 (both the distal and proximal portions 39, 38). The holes are then welded such that a first weld 35 extends through the first hole 28 and a second weld 36 extends through the second hole 29. The first weld 35 attaches the distal portion 39 of the hollow cylindrical member 2 to the malleable tubing 3 at the first end 40 of the malleable tubing 3. The second weld 36 attaches the proximal portion 38 of the hollow cylindrical member 2 to the malleable tubing 3 at the second end 41 of the malleable tubing 3. However, the connection between the proximal portion 38, distal portion 39 and the malleable tubing 3 is not limited to this arrangement. Instead, the connection between the three pieces can include any of those disclosed above such as the radially protruding collars, dimples, shrink-wrap covering, and raised knurled portions.

The illustrated exemplary embodiments of the surgical instrument as set forth above are intended to be illustrative and not limiting. Various changes may be made without departing from the spirit and scope of the invention.

What is claimed is:
1. A surgical instrument comprising:
   a hollow cylindrical member having a distal end, a proximal end, and a flexible region along at least a part of the hollow cylindrical member;
   a malleable tubing disposed over at least an outer surface of the flexible region of the hollow cylindrical member, the malleable tubing having a distal end and a proximal end, the proximal end of the malleable tubing attached to an outer surface of the hollow cylindrical member at a position that is distally spaced from the proximal end of the hollow cylinder member; and
   an inner hollow cylindrical member disposed within the hollow cylindrical member and having a flexible region along at least a part of the inner hollow cylindrical member, wherein
   the flexible region of the hollow cylindrical member and the malleable tubing disposed over the flexible region of the hollow cylindrical member are configured to bend multiple times,
   at least a part of the flexible region of the hollow cylindrical member overlaps at least a part of the flexible region of the inner hollow cylindrical member,
   the malleable tubing is configured to maintain a bent orientation until the malleable tubing is re-bent by a user, and
   the hollow cylindrical member and the inner hollow cylindrical member, excluding the flexible regions, are rigid conduits.

2. The surgical instrument of claim 1, wherein the flexible region of the hollow cylindrical member is formed by at least one helical cut made in the hollow cylindrical member, the at least one helical cut extending around a circumference of the hollow cylindrical member for an entire length of the flexible region.

3. The surgical instrument of claim 1, wherein the malleable tubing is made of an anodized annealed metal or an annealed metal.

4. The surgical instrument of claim 3, wherein the metal is aluminum.

5. The surgical instrument of claim 1, wherein the flexible region of the hollow cylindrical member is formed by at least one helical cut made in the hollow cylindrical member, the at least one helical cut extending around a circumference of the hollow cylindrical member for an entire length of the flexible region.

6. The surgical instrument of claim 1, wherein the malleable tubing is made of aluminum or copper.

7. The surgical instrument of claim 1, wherein the malleable tubing is made of a metal.

8. The surgical instrument of claim 7, wherein the metal is an annealed metal.

9. The surgical instrument of claim 1, wherein the flexible region of the hollow cylindrical member is formed by slits made in the hollow cylindrical member, each of the slits extending partially around a circumference of the hollow cylindrical member without extending entirely around the circumference of the hollow cylindrical member.

10. The surgical instrument of claim 1, wherein the hollow cylindrical member has a hoop strength sufficient to prevent the malleable tubing from flattening when the malleable tubing and the hollow cylindrical member are bent.

11. The surgical instrument of claim 1, further comprising:
connections between the hollow cylindrical member and the malleable tubing to prevent the malleable tubing from moving longitudinally relative to the hollow cylindrical member, the connections located distally and proximally of the flexible region of the hollow cylindrical member.

12. The surgical instrument of claim 11, wherein the connections include:
first dimples formed in the hollow cylindrical member and extending radially inward; and
second dimples formed in the malleable tubing and extending radially inward toward the hollow cylindrical member,
the second dimples extending into the first dimples to fixedly attach the malleable tubing to the hollow cylindrical member.

13. The surgical instrument of claim 11, wherein the connections include:
a first radially protruding collar disposed on the hollow cylindrical member distally of the flexible region of the hollow cylindrical member; and
a second radially protruding collar disposed on the hollow cylindrical member proximally of the flexible region of the hollow cylindrical member, wherein
the malleable tubing is located between the first and second radially protruding collars such that the first radially protruding collar and the second radially protruding collar abut the malleable tubing and restrict axial movement of the malleable tubing with respect to the hollow cylindrical member.

14. The surgical instrument of claim 11, wherein the connections include:
holes extending through the malleable tubing; and
welds extending through the holes and attached to the hollow cylindrical member.

15. The surgical instrument of claim 11, wherein the connections include:
a shrink-wrap covering disposed over at least the malleable tubing and portions of the hollow cylindrical member located distally and proximally of the malleable tubing, wherein
the shrink-wrap covering restricts axial and rotational movement of the malleable tubing with respect to the hollow cylindrical member.

16. The surgical instrument of claim 11, wherein the connections include
raised knurled portions of the hollow cylindrical member, the malleable tubing being friction fitted to the raised knurled portions to restrict axial and rotational movement of the malleable tubing with respect to the hollow cylindrical member.

17. The surgical instrument of claim 11, wherein the connections are adhesive connections.

18. The surgical instrument of claim 1, wherein the hollow cylindrical member is a helical spring.

19. The surgical instrument of claim 1, wherein the hollow cylindrical member includes a cutting window at its distal end and the inner hollow cylindrical member is rotatable within the hollow cylindrical member and includes a cutting window at its distal end, the cutting windows of the hollow cylindrical member and the inner hollow cylindrical member are aligned with each other.

20. The surgical instrument of claim 1, wherein the hollow cylindrical member is a multifilar wire coil having one or more layers.

21. A surgical instrument comprising:
a hollow cylindrical member having a distal end, a proximal end, and a flexible region along at least a part of the hollow cylindrical member;
a malleable tubing disposed over at least an outer surface of the flexible region of the hollow cylindrical member, the malleable tubing having a distal end and a proximal end, the proximal end of the malleable tubing attached to an outer surface of the hollow cylindrical member at a position that is distally spaced from the proximal end of the hollow cylinder member; and
an inner hollow cylindrical member disposed within the hollow cylindrical member and having a flexible region along at least a part of the inner hollow cylindrical member, wherein
the flexible region of the hollow cylindrical member and the malleable tubing disposed over the flexible region of the hollow cylindrical member are configured to bend multiple times,
at least a part of the flexible region of the hollow cylindrical member overlaps at least a part of the flexible region of the inner hollow cylindrical member,
the malleable tubing is configured to maintain a bent orientation until the malleable tubing is re-bent by a user, and
the hollow cylindrical member includes a cutting window at its distal end and the inner hollow cylindrical member is rotatable within the hollow cylindrical member and includes a cutting window at its distal end, the cutting windows of the hollow cylindrical member and the inner hollow cylindrical member are aligned with each other.

* * * * *